United States Patent
Nakamura et al.

(10) Patent No.: US 10,084,947 B2
(45) Date of Patent: Sep. 25, 2018

(54) IMAGING MODULE

(71) Applicant: OLYMPUS CORPORATION, Tokyo (JP)

(72) Inventors: Mikio Nakamura, Tokyo (JP); Nau Satake, Yokohama (JP); Hiroyuki Motohara, Hachioji (JP); Takanori Sekido, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 269 days.

(21) Appl. No.: 14/519,721

(22) Filed: Oct. 21, 2014

(65) Prior Publication Data
US 2015/0035960 A1    Feb. 5, 2015

Related U.S. Application Data

(63) Continuation of application No. PCT/JP2013/059694, filed on Mar. 29, 2013.

(30) Foreign Application Priority Data

Apr. 23, 2012  (JP) .................................. 2012-098006

(51) Int. Cl.
*H01L 29/00*        (2006.01)
*H01L 27/32*        (2006.01)
(Continued)

(52) U.S. Cl.
CPC ....... *H04N 5/2257* (2013.01); *A61B 1/00009* (2013.01); *A61B 1/0011* (2013.01);
(Continued)

(58) Field of Classification Search
CPC .......... H04N 7/18; H04N 9/73; H04N 5/2257; H04N 5/335; H01L 31/101; A61B 1/04
See application file for complete search history.

(56) References Cited

U.S. PATENT DOCUMENTS 8,300,127 B2 * 10/2012 Akiyama .......... H01L 27/14623
257/72
2007/0051988 A1    3/2007 Koga
(Continued)

FOREIGN PATENT DOCUMENTS

JP    63-167319 A    7/1988
JP    07-308284 A    11/1995
(Continued)

OTHER PUBLICATIONS

Japanese Office Action dated Apr. 26, 2016 issued in JP 2012-098006.
(Continued)

*Primary Examiner* — Sathyanaraya V Perungavoor
*Assistant Examiner* — Patricia I Young
(74) *Attorney, Agent, or Firm* — Scully, Scott, Murphy & Presser, P.C.

(57) ABSTRACT

An imaging module includes: an imaging unit including a light receiving unit having a plurality of pixels arranged in a specified shape including a lattice shape and configured to receive light and to perform photoelectric conversion on the received light, the imaging unit being configured to capture an image of a subject and to output the image as a light quantity signal; a signal processing unit configured to perform signal processing on the light quantity signal; and a flexible substrate which includes a bendable insulating film and on which the imaging unit and the signal processing unit are mounted. The flexible substrate is bent to arrange the signal processing unit and the flexible substrate in a space extending from an outer edge of an incident surface of the imaging unit in a direction perpendicular to the incident surface while maintaining a shape of the outer edge.

5 Claims, 7 Drawing Sheets (51) Int. Cl.
  *G02F 1/00* (2006.01)
  *H04N 5/225* (2006.01)
  *A61B 1/00* (2006.01)
  *A61B 1/045* (2006.01)
  *A61B 1/05* (2006.01)
  *H04N 5/378* (2011.01)
  *G03B 17/17* (2006.01)

(52) U.S. Cl.
  CPC .............. *A61B 1/045* (2013.01); *A61B 1/051* (2013.01); *G03B 17/17* (2013.01); *H04N 5/2253* (2013.01); *H04N 5/378* (2013.01); *H04N 2005/2255* (2013.01)

(56) References Cited

U.S. PATENT DOCUMENTS

| | | |
|---|---|---|
| 2008/0185603 A1 | 8/2008 | Itoi et al. |
| 2010/0073470 A1 | 3/2010 | Takasaki |
| 2010/0276572 A1* | 11/2010 | Iwabuchi ............ H01L 27/1464 250/208.1 |
| 2011/0249106 A1 | 10/2011 | Makino et al. |
| 2011/0285003 A1 | 11/2011 | Itoi et al. |
| 2012/0235022 A1 | 9/2012 | Koga |

FOREIGN PATENT DOCUMENTS

| | | |
|---|---|---|
| JP | 2000-209511 A | 7/2000 |
| JP | 2005-193059 A | 7/2005 |
| JP | 2006-055458 A | 3/2006 |
| JP | 2007-068099 A | 3/2007 |
| JP | 2008-219854 A | 9/2008 |
| JP | 2009-170944 A | 7/2009 |
| JP | 2010-069231 A | 4/2010 |
| JP | 2011-217887 A | 11/2011 |

OTHER PUBLICATIONS

International Search Report dated May 7, 2013 issued in PCT/JP2013/059694.

* cited by examiner

IMAGING MODULE

CROSS REFERENCES TO RELATED APPLICATIONS

This application is a continuation of PCT international application Ser. No. PCT/JP2013/059694 filed on Mar. 29, 2013 which designates the United States, incorporated herein by reference, and which claims the benefit of priority from Japanese Patent Application No. 2012-098006, filed on Apr. 23, 2012, incorporated herein by reference.

BACKGROUND

1. Technical Field

The disclosure relates to an imaging module having an imaging unit on which an imaging device is mounted and a signal processing unit configured to perform signal processing on a signal.

2. Related Art

Conventionally, there has appeared an imaging module applicable to various types of devices including not only a digital camera and a digital video camera, but also a mobile phone having an imaging function and an endoscope system for observing the inside of an examinee's organ. Among them, the endoscope system incorporates, at its distal end portion of the flexible and elongate inserting tool, an imaging module including an imaging unit and a signal processing unit. An imaging device having a plurality of pixels is mounted on the imaging unit. The signal processing unit performs signal processing on a light quantity signal imaged by the imaging unit. By inserting the inserting tool into the body cavity, a region to be examined is observed, for example.

The imaging unit includes an optical system such as a lens, and an imaging device such as a CCD image sensor or a CMOS image sensor for generating image data of a subject by performing photoelectric conversion on light with which the optical system forms the image. The image data generated by the imaging unit is output to the signal processing unit as the light quantity signal.

Here, a semiconductor module (imaging module) in which the imaging unit and the signal processing unit are connected by a micro-bump has been proposed, in order to enhance the processing speed at the signal processing unit described above (for example, see JP 2009-170944 A). This imaging module makes it possible to drive and read all pixels or many pixels at the same time, to make the image quality of a display image excellent.

SUMMARY

In some embodiments, an imaging module includes: an imaging unit including a light receiving unit having a plurality of pixels arranged in a specified shape including a lattice shape and configured to receive light and to perform photoelectric conversion on the received light, the imaging unit being configured to capture an image of a subject and to output the image as a light quantity signal; a signal processing unit configured to perform signal processing on the light quantity signal output by the imaging unit; and a flexible substrate which includes a bendable insulating film and on which the imaging unit and the signal processing unit are mounted. The flexible substrate is bent to arrange the signal processing unit and the flexible substrate in a space extending from an outer edge of an incident surface of the imaging unit in a direction perpendicular to the incident surface while maintaining a shape of the outer edge. The imaging unit is configured to perform parallel processing, for each pixel column, on signals output respectively from the plurality of pixels of the light receiving unit and to output the signals as the light quantity signal to an outside of the imaging unit. The signal processing unit is configured to perform parallel signal processing on the light quantity signal for each pixel column and to output the light quantity signal as an imaging signal to an outside of the signal processing unit.

The above and other features, advantages and technical and industrial significance of this invention will be better understood by reading the following detailed description of presently preferred embodiments of the invention, when considered in connection with the accompanying drawings.

DETAILED DESCRIPTION

Exemplary embodiments of the invention will be described below in detail with reference to the drawings. The present invention is not limited to the embodiments described below. Each drawing referred to in the following description only schematically illustrates the shape, size, and positional relation to the extent that the contents of the present invention can be understood. That is, the present invention is not limited only to the shape, size and positional relation illustrated in each drawing.

First Embodiment

Figure 1:
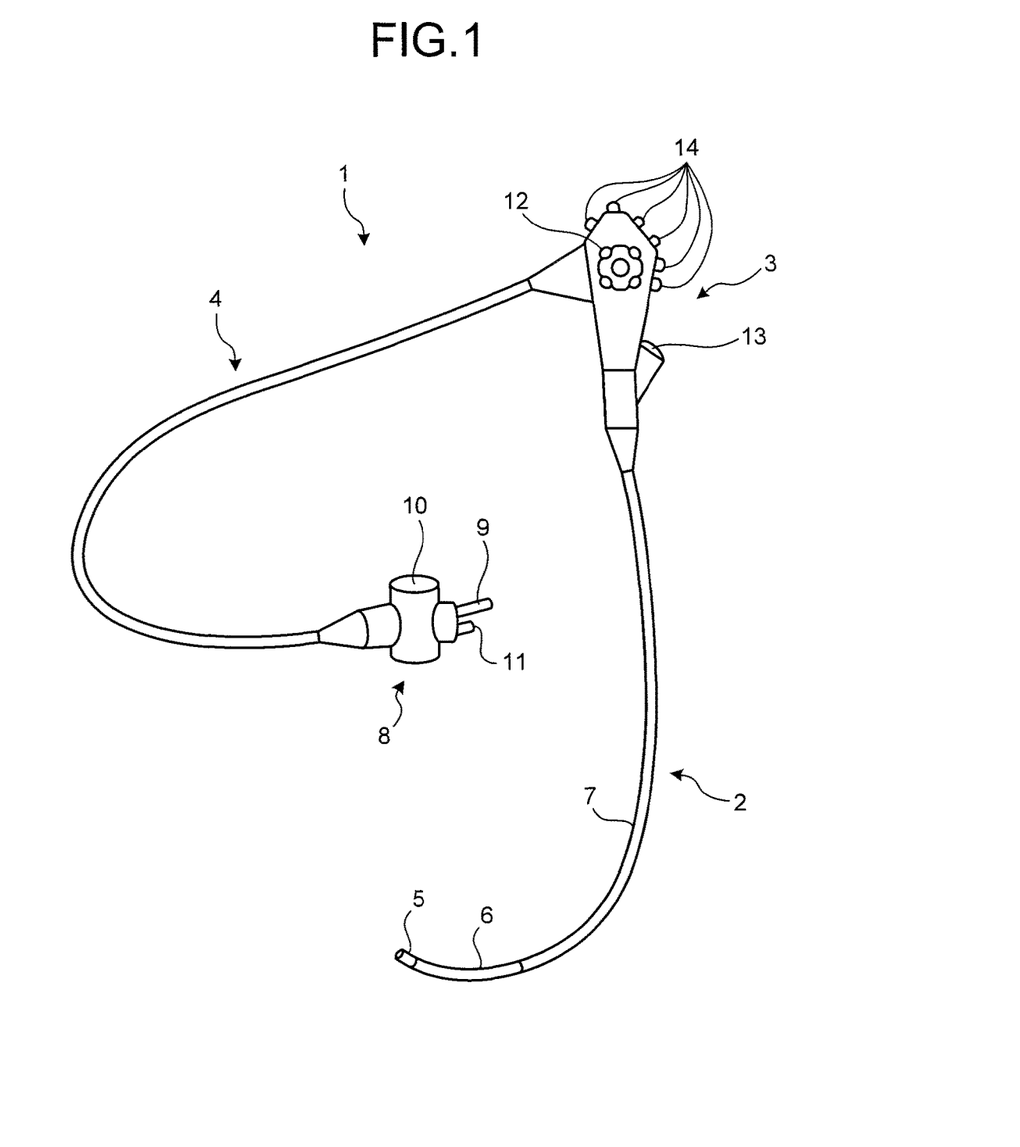
FIG. 1 is a schematic view illustrating the overall configuration of an endoscopic device according to a first embodiment of the present invention.

First, an endoscopic device according to the first embodiment will be described. FIG. 1 is a schematic view illustrating the overall configuration of the endoscopic device 1 according to the first embodiment. As illustrated in FIG. 1, the endoscopic device 1 according to the first embodiment includes an elongate inserting unit 2, an operating unit 3 held by an operator of the endoscopic device at the proximal end side of the inserting unit 2, and a flexible universal cord 4 extending from the side part of the operating unit 3. The universal cord 4 incorporates a light guide cable, an electric system cable, etc.

The inserting unit 2 includes a distal end portion 5, a bending portion 6, and a flexible tube portion 7. The distal end portion 5 incorporates an imaging module having a CMOS image sensor, etc. The bending portion 6 is bendable and includes a plurality of bending pieces. The flexible tube portion 7 is long, flexible, and is provided at the proximal end side of the bending portion 6.

A connector unit 8 is provided at the extended-side end portion of the universal cord 4. The connector unit 8 is provided with a light guide connector 9, an electric contact portion 10, an air-supply cap 11, etc. The light guide connector 9 is detachably connected to a light source device. The electric contact portion 10 is for transmitting, to a signal processing device or a control device, an electric signal of a subject image captured by the imaging module. The air-supply cap 11 is for supplying air to a nozzle of the distal end portion 5. The light source device incorporates a halogen lamp, etc. and supplies light from the halogen lamp as illuminating light to the endoscopic device 1 connected via the light guide connector 9. The signal processing device or the control device is a device which supplies power to the imaging module and to which the photo-electrically converted electric signal is input from the imaging module. The signal processing device or the control device processes the electric signal of the subject image captured by the imaging module, displays an image on the display device to be connected, and outputs a driving signal which controls and drives a gain adjustment, etc. of the imaging module.

The operating unit 3 is provided with a bending knob 12, a treatment tool inserting portion 13, and a plurality of switches 14. The bending knob 12 bends the bending portion 6 in the vertical direction and lateral direction. A treatment tool such as a biopsy forceps or a laser probe is inserted into the body cavity through the treatment tool inserting portion 13. The switches 14 are for operating the signal processing device, the control device, or a peripheral device such as air-supply, water-supply, or gas-supply means. The endoscopic device 1, in which the treatment tool has been inserted into a treatment tool insertion opening, projects a distal end treatment portion of the treatment tool via a treatment tool insertion channel provided inside, and performs, for example, biopsy in which tissue of affected part is collected by a biopsy forceps, etc.

Figure 2:
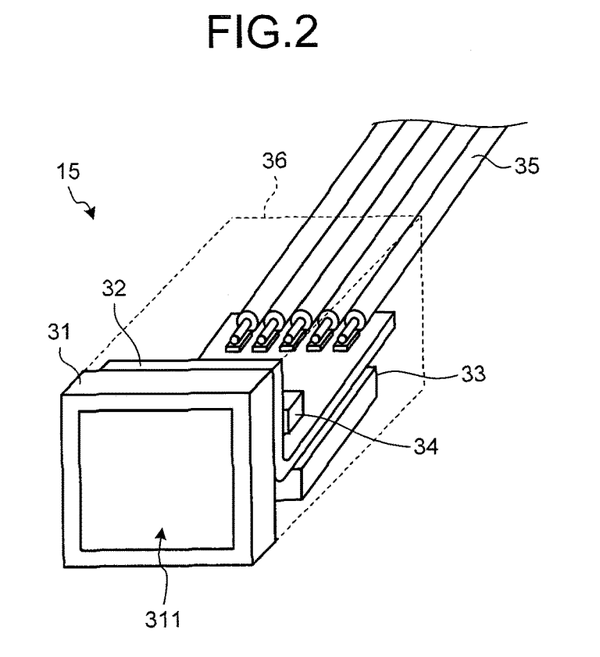
FIG. 2 is a perspective view illustrating an imaging module mounted on a distal end portion of the endoscopic device illustrated in FIG. 1.
Figure 3:
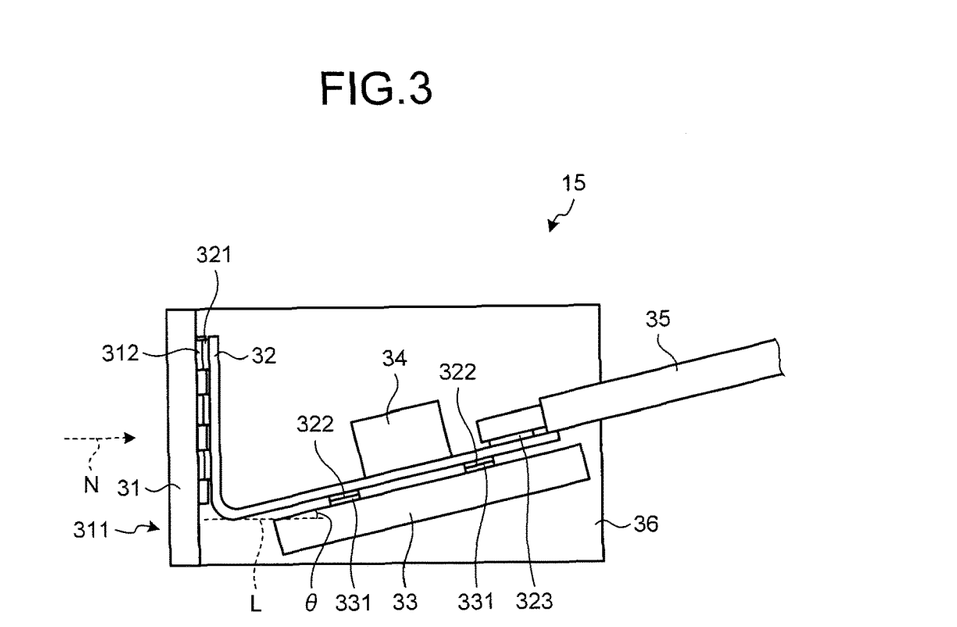
FIG. 3 is a side view schematically illustrating the imaging module illustrated in FIG. 2.
Figure 4:
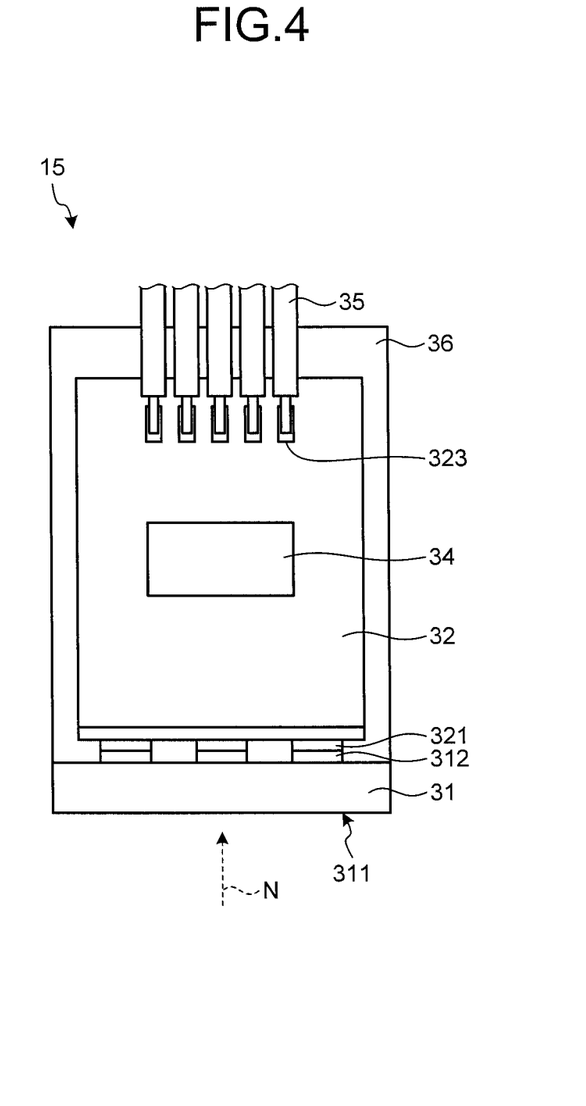
FIG. 4 is a top view schematically illustrating the imaging module illustrated in FIG. 2.

Next, a configuration of an imaging module 15 mounted on the distal end portion 5 of the endoscopic device 1 will be described. FIG. 2 is a perspective view illustrating the imaging module 15 mounted on the distal end portion 5 of the endoscopic device 1 illustrated in FIG. 1. FIG. 3 is a side view schematically illustrating the imaging module 15 mounted on the distal end portion 5 illustrated in FIG. 2. FIG. 4 is a top view schematically illustrating the imaging module 15 mounted on the distal end portion 5 illustrated in FIG. 2.

The imaging module 15 mounted on the distal end portion 5 of the endoscopic device 1 illustrated in FIG. 1 includes at least an imaging unit, a signal processing unit, and a connection unit. The imaging unit includes a pixel chip 31 which receives light from a target to be imaged and performs photoelectric conversion on the received light. The signal processing unit includes a signal processing chip 33 which performs signal processing on a light quantity signal imaged by the imaging unit. The connection unit connects the imaging unit and the signal processing unit. A lens unit (not illustrated) is provided at a light receiving surface side of the pixel chip 31 of the imaging unit. The lens unit has a plurality of lenses in which each center is aligned with an axis N (see FIG. 3). The light condensed by the lens is emitted to the pixel chip 31.

The imaging module 15 illustrated in FIGS. 2 to 4 functions as a general imaging device by the pixel chip 31 and the signal processing chip 33, and has a substantially rectangular parallelepiped shape. The imaging module 15 includes the pixel chip 31, a flexible substrate 32, the substantially plate-shaped signal processing chip 33, a component 34, a wiring cable 35, and an insulating sealing member 36. The pixel chip 31 receives light from the target to be imaged and performs photoelectric conversion on the received light. The flexible substrate 32 is connected to the pixel chip 31 and includes a bendable insulating film. The signal processing chip 33 is connected to the flexible substrate 32 and performs the signal processing of the signal including light quantity information output from the pixel chip 31. The component 34 is mounted on the flexible substrate 32 and has, for example, a capacitor and a circuit for signal control. The wiring cable 35 is connected to the flexible substrate 32 and transmits the imaging signal processed by the signal processing chip 33 to the external signal processing device or the control device. The insulating sealing member 36 is coupled to the other surface of the pixel chip 31, and seals the flexible substrate 32, the signal processing chip 33, the component 34, and at least a connecting part of the wiring cable 35 with the flexible substrate 32 to fix the positional relation among these elements. The imaging module 15 is held by an imaging holder which is formed, for example, of corrosion resistant steel and is disposed at the distal end portion 5.

The pixel chip 31 is a bare chip semiconductor device and has an imaging function of receiving light from a subject to capture an image of the subject. As illustrated in FIG. 3, a light receiving unit 311, which receives light from the subject and performs photoelectric conversion on the received light, is formed on the upper surface of a chip substrate of the pixel chip 31. When the imaging module 15 is completed, the above-described optical axis of the lens unit and a light receiving surface of the light receiving unit 311 are arranged so as to be substantially orthogonal to each other.

The light receiving unit 311 is realized by using, for example, a pixel group including a plurality of pixels arranged in a specified shape such as a lattice shape, and a microlens formed on the pixel group so as to collect light effectively. In addition, the pixel chip 31 includes an external connecting electrode 312 to connect with the outside.

The flexible substrate 32 includes a substantially belt-shaped and bendable insulating film. In the flexible substrate 32, the distance between the opposing sides of this rectangle, more specifically the distance (in the width direction) between one pair of opposing sides, is not longer than the length in the width direction of the principal surface of the pixel chip 31.

The pixel chip 31 and the flexible substrate 32 are electrically connected by connecting the external connecting electrode 312 with an external connecting electrode 321. The flexible substrate 32 and the signal processing chip 33 are electrically connected by connecting an external connecting electrode 322 with an external connecting electrode 331. The pixel chip 31 and the signal processing chip 33 are mounted on the same surface of the flexible substrate 32. The flexible substrate 32 and the wiring cable 35 are electrically connected by connecting an external connecting electrode 323 with a conductor at a tip of the wiring cable 35. Here, on a surface of the flexible substrate 32 opposite to the surface connected to the pixel chip 31 and the signal processing chip 33, the component 34 is mounted and the wiring cable 35 is connected.

Figure 5:
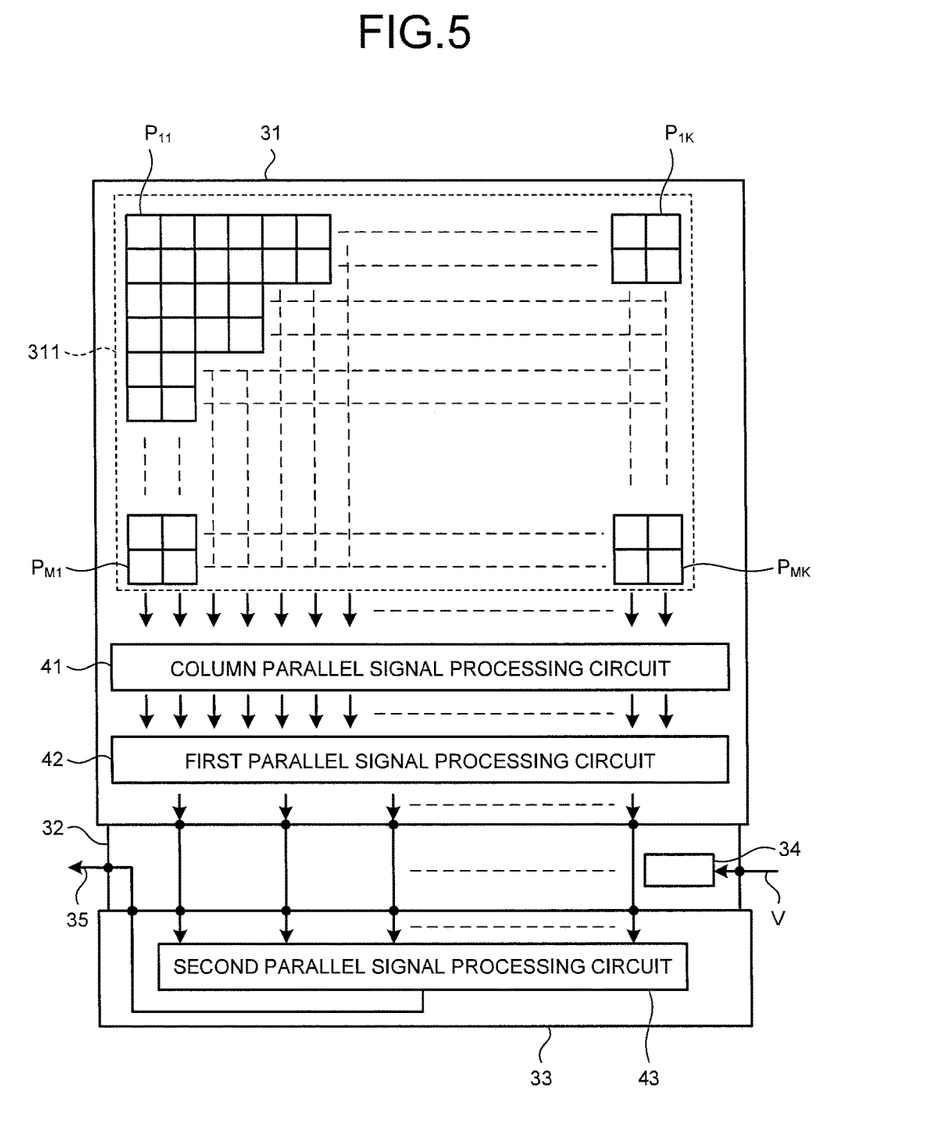
FIG. 5 is a block diagram schematically illustrating a configuration of the imaging module mounted on the distal end portion of the endoscopic device illustrated in FIG. 1.

FIG. 5 is a block diagram schematically illustrating a configuration of the imaging module 15 mounted on the distal end portion 5. The light receiving unit 311 has a plurality of pixels $P_{mk}$ (m=1, 2, 3, ..., M, k=1, 2, 3, ..., K), each of which receives light and performs photoelectric conversion on the received light. Each pixel $P_{mk}$ is arranged in the lattice shape which is represented, for example, as M-by-K matrix, and outputs the photo-electrically converted signal to the outside. The pixel chip 31 includes a column parallel signal processing circuit 41. The column parallel signal processing circuit 41 is provided at 1:1 for the signal of each pixel column k which is output from a plurality of pixels $P_{mk}$ (for example, the signal of the pixel column k for k=1 is the signal output from the pixel $P_{11}$, pixel $P_{21}$ ... $P_{M1}$). The column parallel signal processing circuit 41 performs parallel signal processing on the signal from each pixel column k for each column.

The column parallel signal processing circuit 41 includes at least one circuit, such as a pixel selection switch, an amplifier (Amp), a sample and hold (Sample Hold), or a correlated double sampling (CDS), generally incorporated in the CMOS image sensor, etc. An analog-digital conversion circuit may be included in the column parallel signal processing circuit 41.

In addition, the pixel chip 31 further has a first parallel signal processing circuit 42, which collects signals output from the column parallel signal processing circuit 41 to a plurality of sets and performs the parallel signal processing for each set.

The first parallel signal processing circuit 42 includes at least one circuit, such as the amplifier (Amp), the sample and hold (Sample Hold), or the correlated double sampling (CDS), generally incorporated in the CMOS image sensor, etc. The analog-digital conversion circuit may be included in the first parallel signal processing circuit 42.

In addition, the signal processing chip 33 has a second parallel signal processing circuit 43, which further collects signals from the first parallel signal processing circuit 42 input via the flexible substrate 32 to a plurality of sets and performs the parallel signal processing for each set.

The second parallel signal processing circuit 43 includes at least one circuit, such as the amplifier (Amp), the sample and hold (Sample Hold), or the correlated double sampling (CDS), generally incorporated in the CMOS image sensor, etc. The analog-digital conversion circuit may be included in the second parallel signal processing circuit 43. A power supply V which is supplied to the component 34 is input to the imaging module 15 via the flexible substrate 32.

The pixel chip 31 performs photoelectric conversion on light received in each pixel $P_{mk}$ of the light receiving unit 311, and performs in parallel one or more of the processing such as the amplifier, the sample and hold, or the CDS generally incorporated in the CMOS image sensor, etc., while selecting the pixel columns by the column parallel signal processing circuit 41.

In addition, the pixel chip 31 performs, for each set of a plurality of pixel columns in parallel by the first parallel signal processing circuit 42, one or more of the processing such as the amplifier, the sample and hold, or the CDS generally incorporated in the CMOS image sensor, etc.

As a result, the number of signals output from the first parallel signal processing circuit 42 is reduced compared with the number of pixel columns k. For example, when the signals of three pixel columns are paired as a set and output, the number of signals will be k/3 for the number of signals output from the pixels $P_{mk}$.

The signals processed in parallel for each set of pixel columns by the first parallel signal processing circuit 42 are output to the flexible substrate 32 via the external connecting electrode 312 and the external connecting electrode 321 (see FIG. 3).

The signals of each set of pixel columns output from the first parallel signal processing circuit 42 to the flexible substrate 32, are input to the signal processing chip 33. Then the signal processing chip 33 performs the signal processing of signals for each set of pixel columns. In the signal processing chip 33, the second parallel signal processing circuit 43 performs, on the signals for each set of pixel columns output from the flexible substrate 32, one or more of the parallel signal processing such as the amplifier, the sample and hold, or the CDS generally incorporated in the CMOS image sensor, etc. Then the imaging signal is output to the flexible substrate 32 via the external connecting electrode 322 and the external connecting electrode 331 (see FIG. 3). The imaging signal output to the flexible substrate 32 is output to the outside via the wiring cable 35.

As described above, in the imaging module 15, the imaging signal is generated by performing at least once the processing such as the amplifier, the sample and hold, or the CDS generally incorporated in the CMOS image sensor, etc. by any of the column parallel signal processing circuit 41, the first parallel signal processing circuit 42, and the second parallel signal processing circuit 43.

In this case, the pixel chip 31 outputs the signals for each set of pixel columns in parallel, and the signal processing chip 33 outputs the imaging signal. As a result, since a frequency of the signal output from the pixel chip 31 is lower than a frequency of the signal output from the signal processing chip 33, an effect can be obtained in which the signal deterioration between the pixel chip 31 and the signal processing chip 33 hardly occurs.

Here, as illustrated in FIGS. 3 and 4, the sealing member 36 which seals the flexible substrate 32, the signal processing chip 33, and the component 34 inside the sealing member 36 has, in the rear surface of the light receiving unit 311 of the pixel chip 31, a shape extending in a substantially rectangular parallelepiped shape from a rectangular region. The area of this rectangular region is not greater than that of this rear surface. That is, the flexible substrate 32, the signal processing chip 33, and the component 34 are disposed within a space extending from the outer edge of a surface (incident surface) on which the light receiving unit 311 of the pixel chip 31 is formed, in a direction perpendicular to the incident surface in a cross-sectional shape which maintains this outer edge shape. The cross section of the sealing member 36, which is in parallel with a surface passing through the outer edge of the light receiving surface, has a shape similar to an outer edge shape of the rear surface of the light receiving unit 311, and has a size not larger than the outer edge shape.

In this case, by bending the flexible substrate 32 and by suitably setting the positions of the signal processing chip 33 and the component 34, the flexible substrate 32, the signal processing chip 33, and the component 34 are arranged so as not to project from (i.e., arranged within) the space extending in the direction perpendicular to the incident surface from the rear surface of the light receiving unit 311 of the pixel chip 31 (corresponding to the dashed line in FIG. 2 in the first embodiment). In this case, an angle θ between a principal surface of the signal processing chip 33 and a line segment L parallel with the direction perpendicular to the incident surface (arrow N in FIG. 3) is less than 90°.

A cross section of the sealing member 36, which is in parallel with the light receiving surface of the light receiving unit 311, has an outer edge shape that is the same as an outer edge shape of the pixel chip 31 as illustrated in FIGS. 2 to 4, and more preferably, smaller than the outer edge shape of the pixel chip 31.

According to the first embodiment as described above, in the imaging module 15, at least the signal processing chip 33 and the component 34 are arranged, by bending the flexible substrate 32, in the positions so as not to project from the space extending in the direction perpendicular to the incident surface from the rear surface of the light receiving unit 311 of the pixel chip 31. Therefore, it is possible to obtain a high quality image by the imaging unit and to realize a small imaging module.

In addition, according to the first embodiment as described above, the pixel chip 31 and the signal processing chip 33 are mounted on the same surface of the flexible substrate 32. Therefore, it is not necessary, in mounting the pixel chip 31 and the signal processing chip 33 on the imaging module 15, to turn the flexible substrate 32 over, or to mount the pixel chip 31 and the signal processing chip 33 from the different directions. This makes it possible to simplify the mounting process.

In addition, according to the first embodiment as described above, the flexible substrate 32 including the film is configured to connect to each component. Therefore, it is possible to secure a wide connection region necessary for the connection and to secure a large resin reinforcing area. This makes it possible to firmly connect to each component while keeping the smallness.

Second Embodiment

Figure 6:
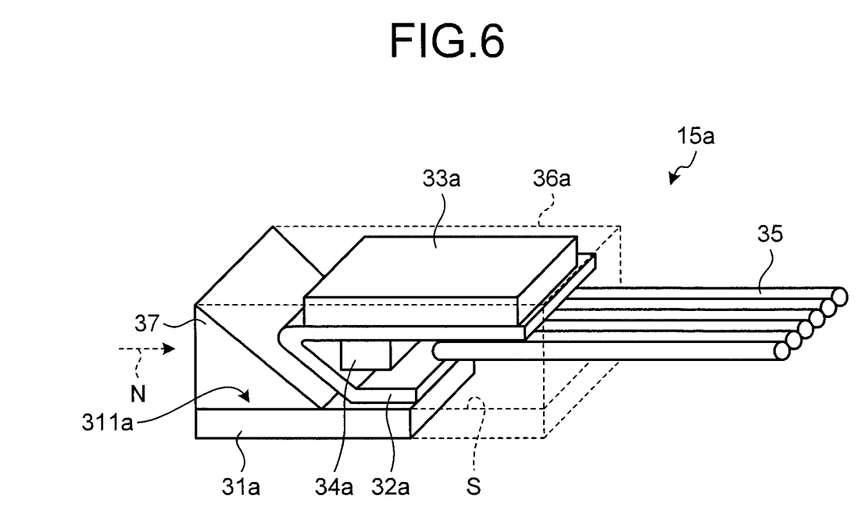
FIG. 6 is a perspective view illustrating an imaging module mounted on a distal end portion of an endoscopic device according to a second embodiment of the present invention.
Figure 7:
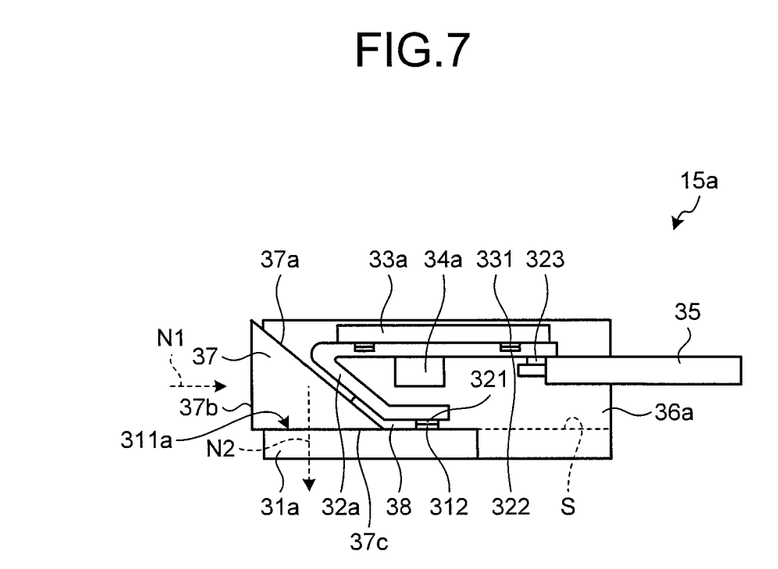
FIG. 7 is a side view schematically illustrating the imaging module illustrated in FIG. 6.

Next, the second embodiment will be described. In the second embodiment, an imaging module having a prism coupled to a light receiving unit 311 in addition to the configuration of the first embodiment described above will be described. FIG. 6 is a perspective view illustrating an imaging module 15a mounted on a distal end portion 5 of an endoscopic device 1 according to the second embodiment. FIG. 7 is a side view schematically illustrating the imaging module 15a illustrated in FIG. 6. The same reference numerals are given to the same components as described above in FIG. 2, etc.

The imaging module 15a includes a pixel chip 31a, a flexible substrate 32a, a signal processing chip 33a, a component 34a, and a sealing member 36a, respectively having a similar configuration and function as the pixel chip 31, the flexible substrate 32, the signal processing chip 33, the component 34, and the sealing member 36 described above. The imaging module 15a also includes a prism 37 placed on a light receiving unit 311a of the pixel chip 31a. The pixel chip 31a and the prism 37 constitute an imaging unit.

The pixel chip 31a is a bare chip semiconductor device and has an imaging function of receiving light from a subject and capturing an image of the subject. As illustrated in FIGS. 6 and 7, the light receiving unit 311a, which receives light from the subject and performs photoelectric conversion on the received light, is formed on the upper surface of a chip substrate of the pixel chip 31a.

The light receiving unit 311a is realized by using, for example, a pixel group including a plurality of pixels arranged in a specified shape such as a lattice shape, and a microlens formed on the pixel group so as to effectively collect light. In addition, the pixel chip 31a includes an external connecting electrode 312 to connect with the outside.

The flexible substrate 32a includes a substantially belt-shaped and bendable insulating film. In the flexible substrate 32a, the distance between the opposing sides of this rectangle, more specifically a distance (in the width direction) between one pair of opposing sides, is not longer than the length in the width direction of a principal surface of the pixel chip 31a.

The pixel chip 31a and the flexible substrate 32a are electrically connected by connecting the external connecting electrode 312 with an external connecting electrode 321. The flexible substrate 32a and the signal processing chip 33a are electrically connected by connecting an external connecting electrode 322 with an external connecting electrode 331. Here, the pixel chip 31a and the signal processing chip 33a are mounted on the same surface of the flexible substrate 32a. The flexible substrate 32a and a wiring cable 35 are electrically connected by connecting an external connecting electrode 323 with a conductor at a tip of the wiring cable 35. Here, on a surface of the flexible substrate 32a opposite to the surface connected to the pixel chip 31a and the signal processing chip 33a, the component 34a is mounted and the wiring cable 35 is connected.

The prism 37 is placed on the light receiving unit 311a of the pixel chip 31a and refracts light from the outside. The prism 37 has a columnar shape extending to form a right triangle in the cross section. Light in an axis N1 direction enters a surface corresponding to one side of the right angle part of this right triangle, and light bent at a right angle inside the prism 37 is emitted in an axis N2 direction from a surface corresponding to the other side. As illustrated in FIG. 7, the prism 37 has an inclined surface portion 37a, an incident surface 37b, and an emission surface 37c. The inclined surface portion 37a corresponds to a hypotenuse of the right triangle. The incident surface 37b corresponds to one side different from the hypotenuse of the right triangle, and light enters the incident surface 37b from the outside. The emission surface 37c corresponds to the other side different from the hypotenuse of the right triangle. Light that has entered from a direction perpendicular to the incident surface 37b and has been reflected from an inner surface (reflection surface) of the prism 37 at the inclined surface portion 37a goes straight and is emitted outside the emission surface 37c.

The prism 37 is stacked on the light receiving unit 311a of the pixel chip 31a such that the emission surface 37c is arranged on the light receiving unit 311a of the pixel chip 31a. The light that has entered the incident surface 37b from the axis N1 direction and has been refracted in the axis N2 direction by the inclined surface portion 37a is emitted from the emission surface 37c and received by the light receiving unit 311a of the pixel chip 31a. On a bottom surface (emission surface 37c) of the prism 37, a recess (not illustrated) is formed to provide an air gap right above the microlens of the light receiving unit 311a.

The flexible substrate 32a is bent along the principal surface of the film such that a height from a contact part with the pixel chip 31a to a tip of the signal processing chip 33a does not exceed a height of the prism 37 under the condition that the prism 37 is stacked on the pixel chip 31a. Here, the flexible substrate 32a has a bent shape extending to the prism 37 side from a connecting part with the pixel chip 31a. Here the flexible substrate 32a is substantially U-shaped which protrudes to the prism 37 side from the side view.

In the imaging module 15a, a reinforcing member 38 is disposed on the coupling side (the connecting part between the external connecting electrode 312 and the external connecting electrode 321) with the pixel chip 31a. The reinforcing member 38 reinforces coupling among the pixel chip 31a, the flexible substrate 32a, and the prism 37. The reinforcing member 38 includes insulating resin. The reinforcing member 38 may not be disposed as long as the pixel chip 31a, the flexible substrate 32a, and the prism 37 are fixed by the sealing member 36a.

The sealing member 36a which seals the flexible substrate 32a, the signal processing chip 33a, and the component 34a inside the sealing member 36a has a shape extending in a substantially rectangular parallelepiped shape from a region formed by a side surface of the pixel chip 31a and the incident surface 37b under the condition that the prism 37 is stacked on the pixel chip 31a. Here, by bending the flexible substrate 32a and by suitably setting the position of the signal processing chip 33a, the flexible substrate 32a, the signal processing chip 33a, and the component 34a are arranged in a space (the space formed by the sealing member 36a and the dashed line S in FIG. 6 and corresponding to a space on the prism 37 side in the second embodiment) extending in the direction perpendicular to the incident surface from the region (outer edge of the incident surface 37b) formed by the side surface of the pixel chip 31a and the incident surface 37b while maintaining the shape of this region, so as not to project from this space. That is, the flexible substrate 32a, the signal processing chip 33a, and the component 34a are arranged in the space extending in the direction perpendicular to the incident surface from the outer edge of the incident surface 37b while maintaining a shape of the outer edge, so as not to project from this space. In the sealing member 36a, the cross-sectional shape parallel with the surface passing through the outer edge of the light receiving surface (the incident surface 37b and the side surface of the pixel chip 31a) is similar to the shape of the outer edge of the region formed by the side surface of the pixel chip 31a and the incident surface 37b and is not larger than the shape of the outer edge.

According to the second embodiment described above, in the imaging module 15a, at least the signal processing chip 33a and the component 34a are arranged in the same manner as the first embodiment, by bending the flexible substrate 32a, in the positions so as not to project from the space extending in the direction perpendicular to the incident surface from the region formed by the side surface of the pixel chip 31a and the incident surface 37b of the prism 37. Therefore, it is possible to obtain a high quality image by the imaging unit and to realize a small imaging module.

Figure 8:
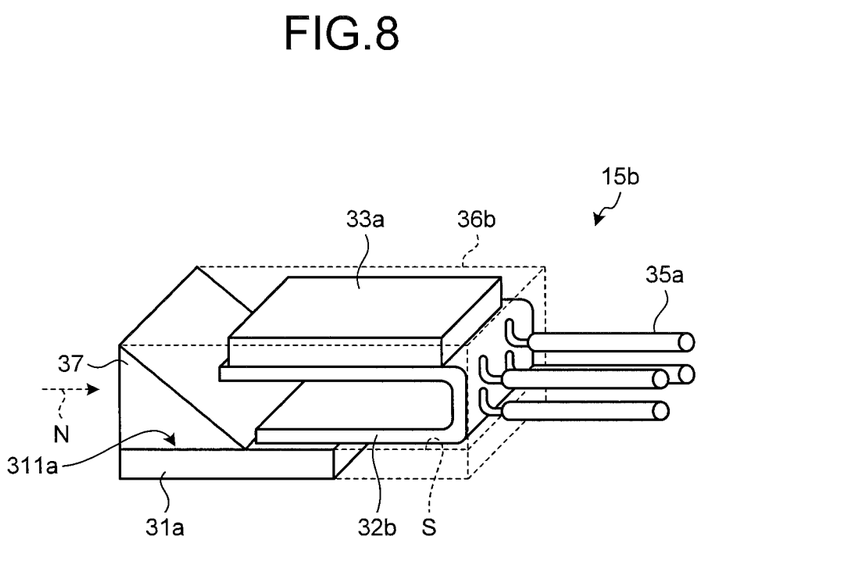
FIG. 8 is a perspective view illustrating an imaging module mounted on a distal end portion of an endoscopic device according to a first modification of the second embodiment of the present invention.
Figure 9:
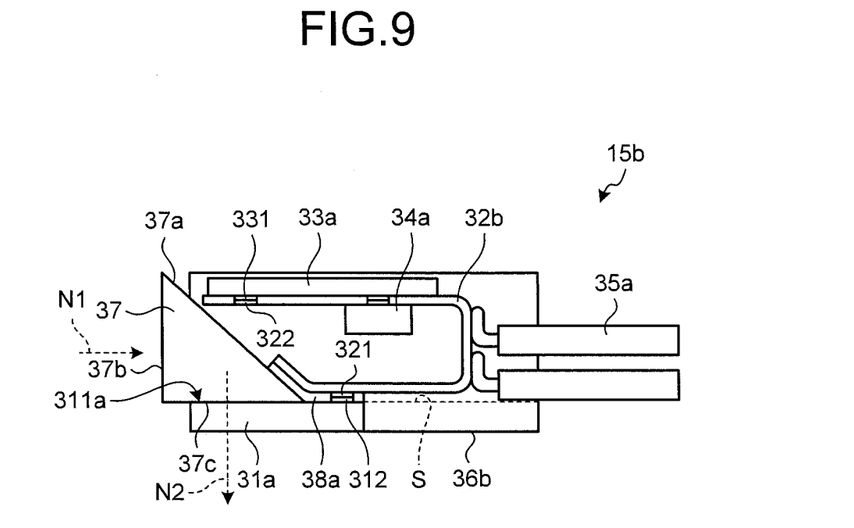
FIG. 9 is a partial sectional view illustrating the imaging module mounted on the distal end portion of the endoscopic device according to the first modification of the second embodiment of the present invention.

FIG. 8 is a perspective view illustrating an imaging module 15b mounted on a distal end portion 5 of an endoscopic device 1 according to a first modification of the second embodiment. FIG. 9 is a partial sectional view illustrating the imaging module 15b mounted on the distal end portion 5 of the endoscopic device 1 according to the first modification of the second embodiment. In the second embodiment described above, the flexible substrate 32a has been described as the bent shape extending to the prism 37 side from the connecting part with the pixel chip 31a. However, a flexible substrate 32b, extending to the opposite side of the prism 37 from a connecting part with a pixel chip 31a as illustrated in FIGS. 8 and 9, may also be used.

The flexible substrate 32b illustrated in FIGS. 8 and 9 includes a substantially belt-shaped and bendable insulating film. The flexible substrate 32b is coupled to the pixel chip 31a at one end side, extends to the opposite side of the prism 37 from the connecting part with the pixel chip 31a, and is connected to a signal processing chip 33a at the other end side. Here the flexible substrate 32b is substantially U-shaped to protrude to the opposite side of the prism 37 from the side view.

A wiring cable 35a is connected to a bent part of the flexible substrate 32b, that is, between the pixel chip 31a and the signal processing chip 33a. Here, a component 34a is connected to the flexible substrate 32b in the inner side.

In the imaging module 15b, a reinforcing member 38a is disposed on the coupling side (the connecting part of an external connecting electrode 312 with an external connecting electrode 321) with the pixel chip 31a to reinforce coupling among the pixel chip 31a, the flexible substrate 32b, and the prism 37. The reinforcing member 38a includes insulating resin. The reinforcing member 38a may not be disposed as long as the pixel chip 31a, the flexible substrate 32b, and the prism 37 are fixed by a sealing member 36b.

The sealing member 36b which seals the flexible substrate 32b, the signal processing chip 33a, and the component 34a inside the sealing member 36b has a shape extending in a substantially rectangular parallelepiped shape from a region formed by a side surface of the pixel chip 31a and the incident surface 37b under the condition that the prism 37 is stacked on the pixel chip 31a. Here, by bending the flexible substrate 32b and by suitably setting the position of the signal processing chip 33a, the flexible substrate 32b, the signal processing chip 33a, and the component 34a are arranged in a space (the space formed by the sealing member 36b and the dashed line S in FIG. 8 and corresponding to a space on the prism 37 side in the first modification) extending in the direction perpendicular to the incident surface from the region formed by the side surface of the pixel chip 31a and the incident surface 37b, so as not to project from this space.

According to the first modification described above, in the imaging module 15b, at least the signal processing chip 33a and the component 34a are arranged in the same manner as the second embodiment, by bending the flexible substrate 32b, in the positions so as not to project from the space extending in the direction perpendicular to the incident surface from the region formed by the side surface of the pixel chip 31a and the incident surface 37b of the prism 37. Therefore, it is possible to obtain a high quality image by the imaging unit and to realize a small imaging module.

Figure 10:
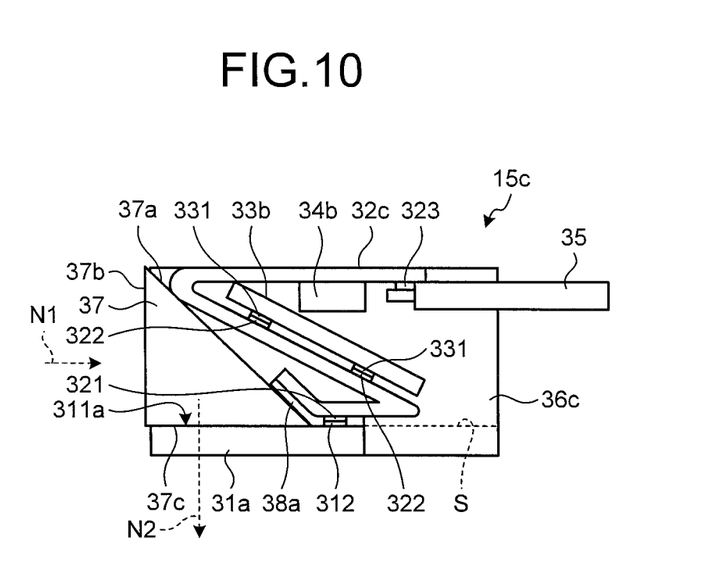
FIG. 10 is a partial sectional view illustrating an imaging module mounted on a distal end portion of an endoscopic device according to a second modification of the second embodiment of the present invention.

FIG. 10 is a partial sectional view illustrating an imaging module 15c mounted on a distal end portion 5 of an endoscopic device 1a according to a second modification of the second embodiment. In the first modification described above, it has been described that the signal processing chip 33a is provided at the belt-shaped end side of the flexible substrate 32b. However, the signal processing chip can be provided at the center part of a flexible substrate 32c as in the second modification illustrated in FIG. 10. Here, a wiring cable 35 is connected to the end portion of the flexible substrate 32c at the side different from the side of a pixel chip 31a. A component 34b having a capacitor, a circuit for signal control and the like is disposed on the same surface as the pixel chip 31a, a signal processing chip 33b, and the wiring cable 35. The flexible substrate 32c, the signal processing chip 33b, and the component 34b are sealed by a sealing member 36c.

In the second modification, since all members can be arranged on the same surface, it is possible to simplify the mounting process for manufacturing the imaging module 15c, in addition to the effect of the first modification.

In the first and second embodiments described above, the sealing member seals the flexible substrate, the signal processing unit, and the component inside the sealing member. However, the sealing member may not be used as long as the positional relation among the flexible substrate, the signal processing unit, and the component can be fixed. In this case, the above-described reinforcing member is preferably disposed.

Although, in the first and second embodiments, reference has been made to a case in which the imaging unit has the pixel group, the column parallel signal processing circuit, and the first parallel signal processing circuit, and the signal processing unit has the second parallel signal processing circuit, it is not limited thereto. The circuit generally incorporated in the CMOS image sensor, etc. may be provided either in the imaging unit or in the signal processing unit. For example, the imaging unit may have the pixel group and the column parallel signal processing circuit, and the signal processing unit may have the first parallel signal processing circuit and the second parallel signal processing circuit.

Although in the first and second embodiments, reference has been made to a case in which the column parallel signal processing circuit outputs the signals for the number of the pixel columns k, and the first parallel signal processing circuit outputs the signals for the number of k/3, the number of the signals paired and output for each column is not limited thereto in both embodiments.

Although in the first and second embodiments, the signal processing unit outputs one imaging signal, a plurality of imaging signals may be output in, for example, a differential signal output format.

Although in the first and second embodiments, an example of the imaging module mounted on the distal end portion of the inserting tool of the endoscopic device has been described, the module can be, of course, applied to an electronic imaging module in various modes including not only a digital camera and a digital video camera, but also a mobile phone having an imaging function.

As described above, the imaging module according to some embodiments is capable of obtaining a high quality image and is useful in realizing a small imaging module.

According to some embodiments, the flexible substrate is bent such that at least the signal processing unit is arranged at a position so as not to project from the space extending from an outer edge of a forming surface of the light receiving unit of the imaging unit or an outer edge of an incident surface of an optical member in a direction perpendicular to the incident surface. Therefore, it is possible to obtain a high quality image and to realize a small imaging module.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging module comprising:
an imaging unit including a light receiving unit comprising a plurality of pixels arranged in a specified shape and configured to receive light and to perform photoelectric conversion on the received light, the imaging unit being configured to capture an image of a subject and to output the image as a light quantity signal;
a signal processing unit configured to output, to an external connecting electrode, an imaging signal generated by performing signal processing on the light quantity signal output by the imaging unit;
a wiring cable connected to the external connecting electrode and configured to output the imaging signal to an outside of the imaging module; and
a flexible substrate which includes a bendable insulating film and on which the imaging unit, the signal processing unit and the wiring cable are mounted,
wherein the flexible substrate is bent to arrange the signal processing unit and the flexible substrate in a space extending from an outer edge of an incident surface of the imaging unit in a first direction perpendicular to the incident surface while maintaining a shape of the outer edge,
wherein the imaging unit is configured to perform parallel processing, for each pixel column, on signals output respectively from the plurality of pixels of the light receiving unit and to output the signals as the light quantity signal to an outside of the imaging unit,
wherein the signal processing unit is configured to perform parallel signal processing on the light quantity signal for each pixel column and to output the light quantity signal as the imaging signal to the external connecting electrode,
wherein the imaging unit and the signal processing unit are mounted on a same surface of the flexible substrate, and
wherein the wiring cable is connected on a surface of the flexible substrate, the surface being an inside surface of the bent flexible substrate and being an opposite side surface of a surface of the flexible substrate on which the flexible substrate is connected to the imaging unit and the signal processing unit.

2. The imaging module according to claim 1, wherein the signal processing unit and the wiring cable are overlapped with each other via the flexible substrate in a second direction that is perpendicular to the first direction and passes through the flexible substrate.

3. The imaging module according to claim 1, wherein the signal processing unit has a substantially plate shape, wherein an angle between a plate surface of the signal processing unit and a line segment parallel with the first direction perpendicular to the incident surface is less than 90°, and wherein the incident surface includes the light receiving unit.

4. The imaging module according to claim 1, wherein the imaging unit includes an optical member comprising:
the incident surface;
a reflection surface configured to reflect light which has entered from the incident surface; and
an emission surface arranged on the light receiving unit and configured to emit light, which has entered from the direction perpendicular to the incident surface and has been reflected from the reflection surface, straight to the outside of the optical member.

5. The imaging module according to claim 1, further comprising a sealing member which seals the signal processing unit and the flexible substrate inside the sealing member, wherein a cross section of the sealing member parallel with a surface passing through the outer edge has a shape similar to that of the outer edge and has a size not larger than the shape of the outer edge.

* * * * *